US012746345B2

(12) United States Patent
Chattaraj et al.

(10) Patent No.: US 12,746,345 B2

(45) Date of Patent: *Sep. 29, 2026

(54) FLUID CONDUIT ASSEMBLY WITH GAS TRAPPING FILTER IN THE FLUID FLOW PATH

(71) Applicant: MEDTRONIC MINIMED, INC., Northridge, CA (US)

(72) Inventors: Sarnath Chattaraj, Simi Valley, CA (US); Kiem H. Dang, Thousand Oaks, CA (US); Poonam S. Gulati, La Canada, CA (US); Guangping Zhang, Calabasas, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 18/469,739

(22) Filed: Sep. 19, 2023

(65) Prior Publication Data

US 2024/0001046 A1 Jan. 4, 2024

Related U.S. Application Data

(63) Continuation of application No. 17/374,226, filed on Jul. 13, 2021, now Pat. No. 11,786,673, which is a (Continued)

(51) Int. Cl.

| | |
|---|---|
| ***A61M 5/38*** | (2006.01) |
| ***A61M 5/142*** | (2006.01) |

(Continued)

(52) U.S. Cl.

CPC .............. *A61M 5/38* (2013.01); *A61M 5/142* (2013.01); *A61M 5/14244* (2013.01); *A61M 5/162* (2013.01); *A61M 39/10* (2013.01)

(58) Field of Classification Search

CPC ...... A61M 2005/1403; A61M 2205/12; A61M 5/36; A61M 5/38; A61M 2205/7527;

(Continued)

(56) References Cited

U.S. PATENT DOCUMENTS

| | | | |
|---|---|---|---|
| 3,003,500 | A | 10/1961 | Barton et al. |
| 3,631,654 | A | 1/1972 | Riely et al. |

(Continued)

FOREIGN PATENT DOCUMENTS

| | | | |
|---|---|---|---|
| CN | 1583188 | A | 2/2005 |
| CN | 1795932 | A | 7/2006 |

(Continued)

*Primary Examiner* — Scott J Medway

(74) *Attorney, Agent, or Firm* — Fortem IP LLP

(57) ABSTRACT

A fluid delivery system and a fluid conduit assembly suitable for use with the system are disclosed herein. The system includes a fluid infusion pump and a fluid conduit assembly coupled to the pump to deliver medication fluid to a user. The fluid conduit assembly includes a structure defining a flow path for the medication fluid, and a gas trapping filter coupled to the structure and positioned in the flow path. The gas trapping filter functions to filter particulates from the medication fluid and retain gas bubbles from the medication fluid.

12 Claims, 6 Drawing Sheets

Related U.S. Application Data continuation of application No. 16/368,630, filed on Mar. 28, 2019, now Pat. No. 11,090,446, which is a continuation of application No. 14/508,934, filed on Oct. 7, 2014, now Pat. No. 10,279,126.

(51) Int. Cl.
*A61M 5/162* (2006.01)
*A61M 39/10* (2006.01)

(58) Field of Classification Search
CPC .......... A61M 2205/7536; A61M 5/385; A61M 2005/1657; B01D 19/0031; B01D 46/0012
See application file for complete search history.

(56) References Cited

U.S. PATENT DOCUMENTS 3,650,093 A 3/1972 Rosenberg
3,827,562 A 8/1974 Esmond
3,882,026 A 5/1975 McPhee
3,978,857 A 9/1976 McPhee
4,004,587 A 1/1977 Jess
4,013,072 A 3/1977 Jess
4,116,646 A 9/1978 Edwards
4,190,426 A 2/1980 Ruschke
4,459,139 A 7/1984 Vonreis et al.
4,562,751 A 1/1986 Nason et al.
4,571,244 A 2/1986 Knighton
4,678,408 A 7/1987 Nason et al.
4,685,903 A 8/1987 Cable et al.
4,755,173 A 7/1988 Konopka et al.
4,804,360 A 2/1989 Kamen
5,080,653 A 1/1992 Voss et al.
5,097,122 A 3/1992 Colman et al.
5,183,472 A 2/1993 Jaehrling et al.
5,195,986 A 3/1993 Kamen
5,308,333 A 5/1994 Skakoon
5,391,250 A 2/1995 Cheney et al.
5,472,435 A 12/1995 Sutton
5,485,408 A 1/1996 Blomquist
5,505,709 A 4/1996 Funderburk et al.
5,522,769 A 6/1996 Deguiseppi
5,522,803 A 6/1996 Teissen-Simony
5,665,065 A 9/1997 Colman et al.
5,800,420 A 9/1998 Gross et al.
5,807,375 A 9/1998 Gross et al.
5,902,281 A 5/1999 Kraus et al.
5,925,021 A 7/1999 Castellano et al.
5,954,643 A 9/1999 Vanantwerp et al.
6,017,328 A 1/2000 Fischell et al.
6,186,982 B1 2/2001 Gross et al.
6,246,992 B1 6/2001 Brown
6,248,067 B1 6/2001 Causey et al.
6,248,093 B1 6/2001 Moberg
6,355,021 B1 3/2002 Nielsen et al.
6,376,211 B1 4/2002 Little et al.
6,379,301 B1 4/2002 Worthington et al.
6,471,689 B1 10/2002 Joseph et al.
6,485,465 B2 11/2002 Moberg et al.
6,544,212 B2 4/2003 Galley et al.
6,554,798 B1 4/2003 Mann et al.
6,558,351 B1 5/2003 Steil et al.
6,591,876 B2 7/2003 Safabash
6,641,533 B2 11/2003 Causey et al.
6,659,980 B2 12/2003 Moberg et al.
6,736,797 B1 5/2004 Larsen et al.
6,749,587 B2 6/2004 Flaherty
6,752,787 B1 6/2004 Causey et al.
6,766,183 B2 7/2004 Walsh et al.
6,801,420 B2 10/2004 Talbot et al.
6,804,544 B2 10/2004 Van Antwerp et al.
6,817,990 B2 11/2004 Yap et al.
6,932,584 B2 8/2005 Gray et al.
6,977,105 B1 12/2005 Fujieda et al.
7,003,336 B2 2/2006 Holker et al.
7,029,444 B2 4/2006 Shin et al.
7,066,909 B1 6/2006 Peter et al.
7,137,390 B2 * 11/2006 Fudge ................ A61M 16/085 128/205.12
7,137,964 B2 11/2006 Flaherty
7,270,693 B2 * 9/2007 Chung ............... B01D 39/1623 55/528
7,303,549 B2 12/2007 Flaherty et al.
7,399,277 B2 7/2008 Saidara et al.
7,442,186 B2 10/2008 Blomquist
7,602,310 B2 10/2009 Mann et al.
7,621,893 B2 11/2009 Moberg et al.
7,647,237 B2 1/2010 Malave et al.
7,699,807 B2 4/2010 Faust et al.
7,727,148 B2 6/2010 Talbot et al.
7,785,313 B2 8/2010 Mastrototaro
7,806,886 B2 10/2010 Kanderian et al.
7,819,843 B2 10/2010 Mann et al.
7,828,764 B2 11/2010 Moberg et al.
7,879,010 B2 2/2011 Hunn et al.
7,890,295 B2 2/2011 Shin et al.
7,892,206 B2 2/2011 Moberg et al.
7,892,748 B2 2/2011 Norrild et al.
7,901,394 B2 3/2011 Ireland et al.
7,942,844 B2 5/2011 Moberg et al.
7,946,985 B2 5/2011 Mastrototaro et al.
7,955,305 B2 6/2011 Moberg et al.
7,963,954 B2 6/2011 Kavazov
7,977,112 B2 7/2011 Burke et al.
7,979,259 B2 7/2011 Brown
7,985,330 B2 7/2011 Wang et al.
8,024,201 B2 9/2011 Brown
8,100,852 B2 1/2012 Moberg et al.
8,114,268 B2 2/2012 Wang et al.
8,114,269 B2 2/2012 Cooper et al.
8,137,314 B2 3/2012 Mounce et al.
8,181,849 B2 5/2012 Bazargan et al.
8,182,462 B2 5/2012 Istoc et al.
8,192,395 B2 6/2012 Estes et al.
8,195,265 B2 6/2012 Goode et al.
8,202,250 B2 6/2012 Stutz
8,207,859 B2 6/2012 Enegren et al.
8,226,615 B2 7/2012 Bikovsky
8,257,259 B2 9/2012 Brauker et al.
8,267,921 B2 9/2012 Yodfat et al.
8,275,437 B2 9/2012 Brauker et al.
8,277,415 B2 10/2012 Mounce et al.
8,292,849 B2 10/2012 Bobroff et al.
8,298,172 B2 10/2012 Nielsen et al.
8,303,572 B2 11/2012 Adair et al.
8,305,580 B2 11/2012 Aasmul
8,308,679 B2 11/2012 Hanson et al.
8,313,433 B2 11/2012 Cohen et al.
8,318,443 B2 11/2012 Norrild et al.
8,323,250 B2 12/2012 Chong et al.
8,343,092 B2 1/2013 Rush et al.
8,352,011 B2 1/2013 Van Antwerp et al.
8,353,829 B2 1/2013 Say et al.
9,901,514 B2 2/2018 Kavazov
10,279,126 B2 5/2019 Chattaraj et al.
11,090,446 B2 8/2021 Chattaraj et al.
11,197,949 B2 12/2021 Dang et al.
11,786,673 B2 10/2023 Chattaraj et al.
12,201,752 B2 1/2025 Dang et al.
12,208,181 B2 1/2025 Dang et al.
2002/0077598 A1 6/2002 Yap et al.
2002/0173748 A1 11/2002 McConnell et al.
2003/0032945 A1 2/2003 Jayaraman
2003/0044555 A1 3/2003 Ding et al.
2003/0060801 A1 3/2003 Chong et al.
2003/0100563 A1 5/2003 Edmondson et al.
2005/0161042 A1 7/2005 Fudge et al.
2006/0058737 A1 3/2006 Herweck et al.
2006/0229530 A1 10/2006 Hosoda et al.
2006/0246272 A1 11/2006 Zhang et al.
2007/0123819 A1 5/2007 Mernoe et al.
2007/0125374 A1 6/2007 Smith et al.

(56) References Cited

U.S. PATENT DOCUMENTS

| | | | |
|---|---|---|---|
| 2007/0225746 A1 | 9/2007 | Lee et al. | |
| 2008/0097407 A1 | 4/2008 | Plishka | |
| 2008/0105618 A1 | 5/2008 | Beckius et al. | |
| 2008/0200903 A1 * | 8/2008 | Christensen .......... | A61M 39/20 604/537 |
| 2009/0192447 A1 * | 7/2009 | Andersen ................ | A61M 5/40 607/96 |
| 2010/0160861 A1 | 6/2010 | Causey et al. | |
| 2010/0234824 A1 | 9/2010 | Christoph et al. | |
| 2011/0184382 A1 | 7/2011 | Cady | |
| 2013/0303987 A1 | 11/2013 | Esnouf | |
| 2014/0228806 A1 | 8/2014 | Alisantoso et al. | |
| 2015/0112302 A1 | 4/2015 | Chattaraj et al. | |
| 2015/0367098 A1 | 12/2015 | Aggerholm et al. | |
| 2016/0095987 A1 | 4/2016 | Chattaraj et al. | |
| 2016/0339226 A1 | 11/2016 | Sealfon | |
| 2016/0375104 A1 | 12/2016 | Joseph et al. | |
| 2017/0143950 A1 | 5/2017 | Koch et al. | |
| 2021/0093775 A1 | 4/2021 | Jezek et al. | |
| 2021/0338943 A1 | 11/2021 | Chattaraj et al. | |
| 2022/0031941 A1 | 2/2022 | Dang et al. | |
| 2022/0409777 A1 | 12/2022 | Dang et al. | |
| 2023/0108058 A1 | 4/2023 | Dang et al. | |
| 2025/0108150 A1 | 4/2025 | Dang et al. | |

FOREIGN PATENT DOCUMENTS

| | | | |
|---|---|---|---|
| CN | 201969126 | U | 9/2011 |
| CN | 103100131 | A | 5/2013 |
| CN | 103418053 | A | 12/2013 |
| CN | 105848693 | A | 8/2016 |
| EP | 2229970 | A1 | 9/2010 |
| EP | 3570932 | A1 | 11/2019 |
| WO | 2012033847 | A1 | 3/2012 |
| WO | 2015061493 | A1 | 4/2015 |
| WO | 2016057093 | A1 | 4/2016 |
| WO | 2018136799 | A1 | 7/2018 |

* cited by examiner

FLUID CONDUIT ASSEMBLY WITH GAS TRAPPING FILTER IN THE FLUID FLOW PATH

CROSS-REFERENCE TO RELATED APPLICATION

This application is a continuation of U.S. patent application Ser. No. 17/374,226, filed Jul. 13, 2021, which is a continuation of U.S. patent application Ser. No. 16/368,630, filed Mar. 28, 2019, now U.S. Pat. No. 11,090,446, which is a continuation of U.S. patent application Ser. No. 14/508,934, filed Oct. 7, 2014, now U.S. Pat. No. 10,279,126.

TECHNICAL FIELD

Embodiments of the subject matter described herein relate generally to fluid infusion devices for delivering a medication fluid to the body of a user. More particularly, embodiments of the subject matter relate to the use of a gas trapping filter in the medication fluid flow path.

BACKGROUND

Certain diseases or conditions may be treated, according to modern medical techniques, by delivering a medication fluid or other substance to the body of a patient, either in a continuous manner or at particular times or time intervals within an overall time period. For example, diabetes is commonly treated by delivering defined amounts of insulin to the patient at appropriate times. Some common modes of providing insulin therapy to a patient include delivery of insulin through manually operated syringes and insulin pens. Other modern systems employ programmable fluid infusion devices (e.g., continuous insulin infusion devices such as insulin pumps) to deliver controlled amounts of insulin or other drugs to a patient.

A fluid infusion device suitable for use as an insulin pump may be realized as an external device or an implantable device, which is surgically implanted into the body of the patient. External fluid infusion devices include devices designed for use in a generally stationary location (for example, in a hospital or clinic), and devices configured for ambulatory or portable use (to be carried by a patient). External fluid infusion devices may establish a fluid flow path from a fluid reservoir to the patient via, for example, a suitable hollow tubing. The hollow tubing may be connected to a hollow fluid delivery needle that is designed to pierce the patient's skin to deliver an infusion fluid to the body. Alternatively, the hollow tubing may be connected directly to the patient's body through a cannula or set of micro-needles.

It is desirable to reduce the amount of air bubbles in a medication fluid before delivering the fluid to the patient. Small bubbles may be introduced into the medication fluid during a reservoir filling operation, for example, when the fluid reservoir is filled from a vial using a syringe. Although patients are instructed to eliminate air from a filled reservoir, some micro bubbles may remain.

Accordingly, it is desirable to have an assembly, system, or component that is designed to mitigate the effects of air bubbles within a medication fluid flow path. In addition, it is desirable to have an assembly, system, or component that reduces the presence of air bubbles in a fluid flow path while also filtering particulates and/or unwanted substances from the medication fluid. Furthermore, other desirable features and characteristics will become apparent from the subsequent detailed description and the appended claims, taken in conjunction with the accompanying drawings and the foregoing technical field and background.

BRIEF SUMMARY

Disclosed herein is a fluid conduit assembly for delivery of a medication fluid. An exemplary embodiment of the fluid conduit assembly includes a structure defining a flow path for the medication fluid and a gas trapping filter coupled to the structure. The gas trapping filter is positioned in the flow path to filter particulates from the medication fluid and retain gas bubbles from the medication fluid.

A fluid delivery system is also disclosed herein. An exemplary embodiment of the system includes: a fluid infusion pump to provide a medication fluid; a fluid conduit assembly coupled to the fluid infusion pump; and a gas trapping filter. The fluid conduit delivers the medication fluid to a user, and the fluid conduit assembly defines a flow path for the medication fluid. The gas trapping filter is positioned in the flow path to filter particulates from the medication fluid and retain gas bubbles from the medication fluid.

Also disclosed herein is a fluid conduit assembly for delivery of a medication fluid. An exemplary embodiment of the fluid conduit assembly includes a body section to receive a fluid reservoir, and a flow path defined in the body section. The flow path carries fluid from the fluid reservoir when the body section is coupled to the fluid reservoir. The fluid conduit assembly also has a length of tubing extending from the body section and in fluid communication with the flow path. The length of tubing carries fluid from the body section during a fluid delivery operation. The fluid conduit assembly also has a partially or predominantly hydrophilic gas trapping filter positioned in the flow path to filter particulates from the medication fluid and retain gas bubbles from the medication fluid.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter described here relates to certain assemblies, components, and features of a fluid infusion system of the type used to treat a medical condition of a patient. The fluid infusion system is used for infusing a medication fluid into the body of a user. The non-limiting examples described below relate to a medical device used to treat diabetes (more specifically, an insulin pump), although embodiments of the disclosed subject matter are not so limited. Accordingly, the medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. Moreover, the gas trapping filter described below could be utilized in the context of other fluid delivery systems if so desired.

For the sake of brevity, conventional features and technologies related to infusion system operation, insulin pump and/or infusion set operation, and other functional aspects of the fluid infusion system (and the individual operating components of the system) may not be described in detail here. Examples of infusion pumps and/or related pump drive systems used to administer insulin and other medications may be of the type described in, but not limited to, U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; and 7,621,893; which are herein incorporated by reference.

Figure 1:
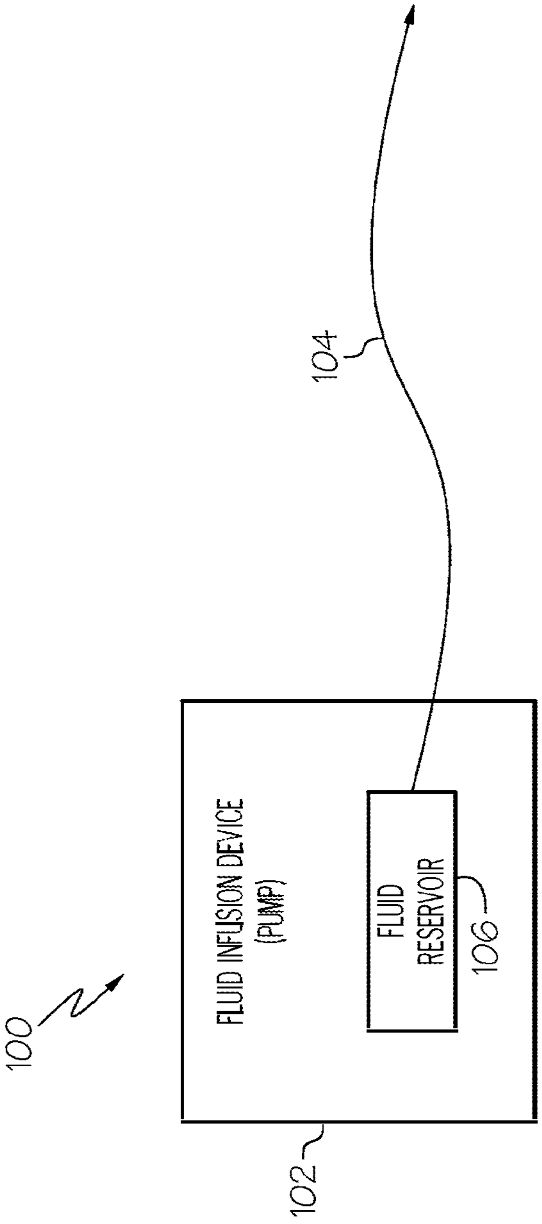
FIG. 1 is a simplified block diagram representation of an embodiment of a fluid delivery system.

FIG. 1 is a simplified block diagram representation of an embodiment of a fluid delivery system 100, which can be utilized to administer a medication fluid such as insulin to a patient. The fluid delivery system 100 includes a fluid infusion device 102 (e.g., an infusion pump) and a fluid conduit assembly 104 that is coupled to, integrated with, or otherwise associated with the fluid infusion device 102. The fluid infusion device 102 includes a fluid reservoir 106 or an equivalent supply of the medication fluid to be administered. The fluid infusion device 102 is operated in a controlled manner to deliver the medication fluid to the user via the fluid conduit assembly 104. Although not depicted in FIG. 1, the fluid delivery system 100 also includes a gas trapping filter that is positioned in the fluid flow path. In certain embodiments, the gas trapping filter is located within the fluid flow path defined by the fluid conduit assembly 104.

Figure 2:
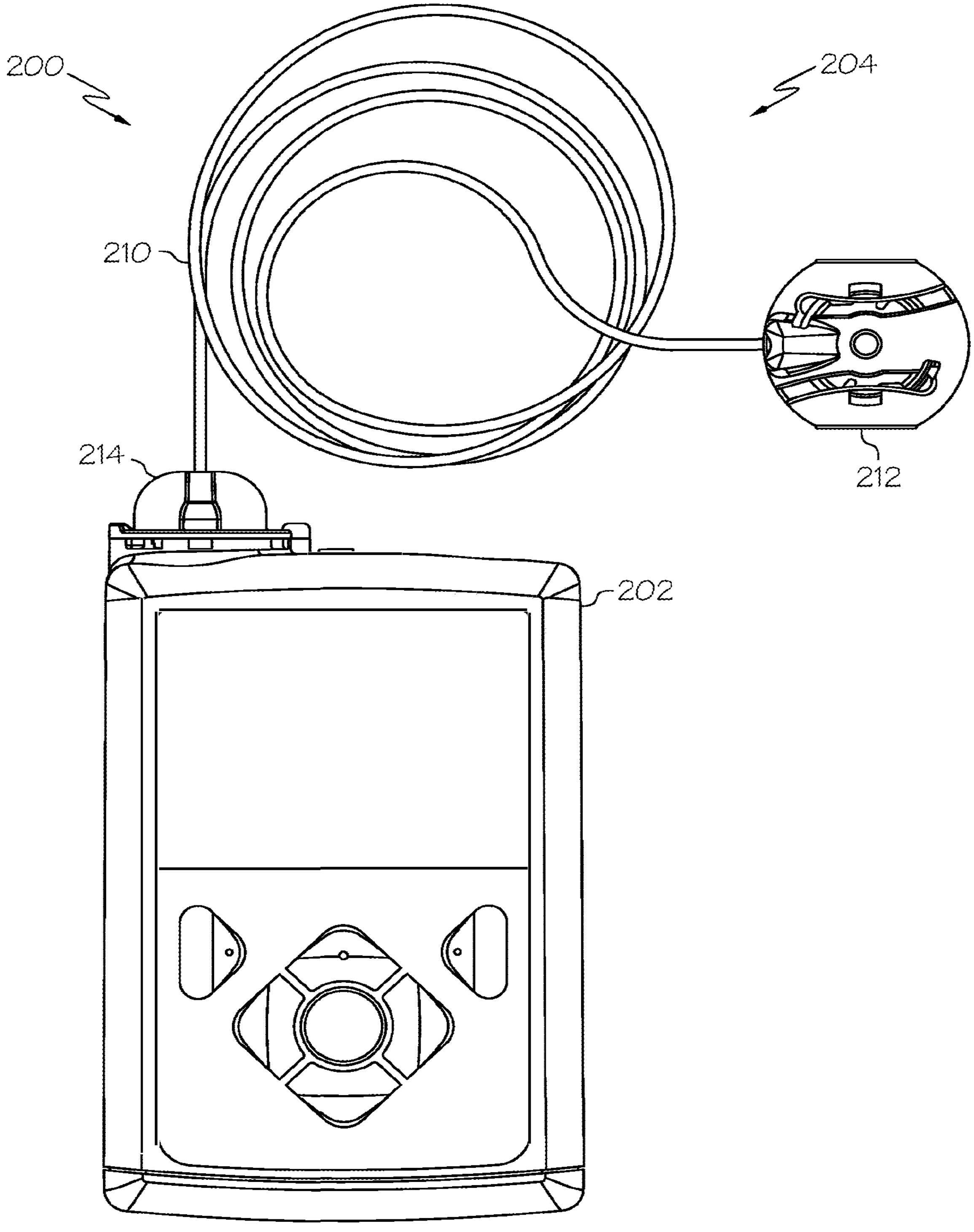
FIG. 2 is a plan view of an exemplary embodiment of a fluid delivery system that includes a fluid infusion device and an infusion set.

The fluid infusion device 102 may be provided in any desired configuration or platform. In accordance with one non-limiting embodiment, the fluid infusion device is realized as a portable unit that can be carried or worn by the patient. In this regard, FIG. 2 is a plan view of an exemplary embodiment of a fluid delivery system 200 that includes a portable fluid infusion device 202 and a fluid conduit assembly that takes the form of an infusion set component 204. For this particular embodiment, the infusion set component 204 can be coupled to the fluid infusion device 202 as depicted in FIG. 2. The fluid infusion device 202 accommodates a fluid reservoir (hidden from view in FIG. 2) for the medication fluid to be delivered to the user.

The illustrated embodiment of the infusion set component 204 includes, without limitation: a tube 210; an infusion unit 212 coupled to the distal end of the tube 210; and a connector assembly 214 coupled to the proximal end of the tube 210. The fluid infusion device 202 is designed to be carried or worn by the patient, and the infusion set component 204 terminates at the infusion unit 212 such that the fluid infusion device 202 can deliver fluid to the body of the patient via the tube 210. The fluid infusion device 202 may leverage a number of conventional features, components, elements, and characteristics of existing fluid infusion devices. For example, the fluid infusion device 202 may incorporate some of the features, components, elements, and/or characteristics described in U.S. Pat. Nos. 6,485,465 and 7,621,893, the relevant content of which is incorporated by reference herein.

The infusion set component 204 defines a fluid flow path that fluidly couples the fluid reservoir to the infusion unit 212. The connector assembly 214 mates with and couples to the neck region of the fluid reservoir, establishing the fluid path from the fluid reservoir to the tube 210. The connector assembly 214 (with the fluid reservoir coupled thereto) is coupled to the housing of the fluid infusion device 202 to seal and secure the fluid reservoir inside the housing. Thereafter, actuation of the fluid infusion device 202 causes the medication fluid to be expelled from the fluid reservoir, through the infusion set component 204, and into the body of the patient via the infusion unit 212 at the distal end of the tube 210. Accordingly, when the connector assembly 214 is installed as depicted in FIG. 2, the tube 210 extends from the fluid infusion device 202 to the infusion unit 212, which in turn provides a fluid pathway to the body of the patient. For the illustrated embodiment, the connector assembly 214 is realized as a removable reservoir cap (or fitting) that is suitably sized and configured to accommodate replacement of fluid reservoirs (which are typically disposable) as needed.

Figure 3:
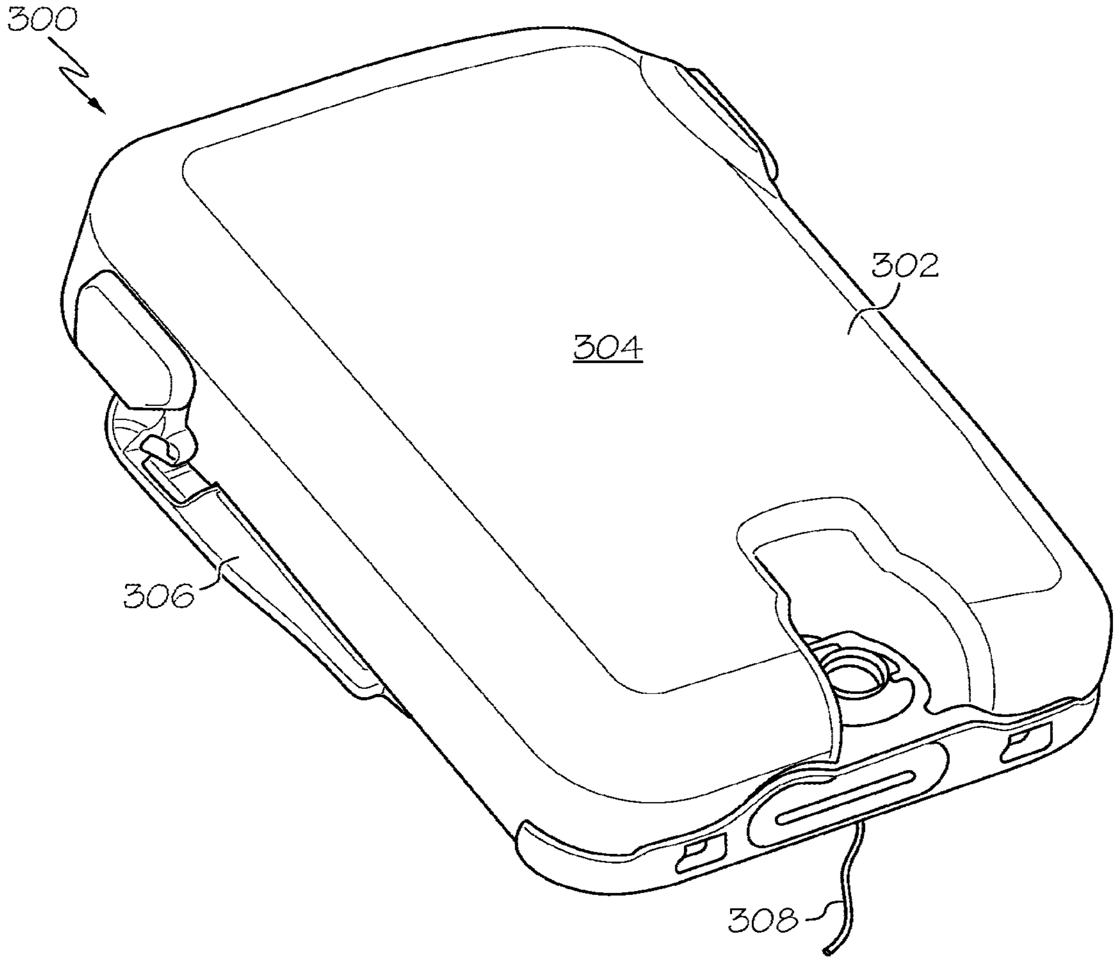
FIG. 3 is a perspective view of an exemplary embodiment of a fluid delivery system that includes a fluid infusion device designed to be affixed to the skin of the user.

FIG. 3 is a perspective view of another exemplary embodiment of a fluid delivery system 300 that includes a fluid infusion device 302 designed to be affixed to the skin of the user. The fluid infusion device 302 includes two primary components that are removably coupled to each other: a durable housing 304; and a base plate 306. The fluid infusion device 302 also includes or cooperates with a removable/replaceable fluid reservoir (which is hidden from view in FIG. 3). For this particular embodiment, the fluid reservoir mates with, and is received by, the durable housing 304. In alternate embodiments, the fluid reservoir mates with, and is received by, the base plate 306.

The base plate 306 is designed to be temporarily adhered to the skin of the patient using, for example, an adhesive layer of material. After the base plate is affixed to the skin of the patient, a suitably configured insertion device or apparatus may be used to insert a fluid delivery needle or cannula 308 into the body of the patient. The cannula 308 functions as one part of the fluid delivery flow path associated with the fluid infusion device 302. In this regard, the cannula 308 may be considered to be one implementation of the fluid conduit assembly 104 shown in FIG. 1 (or a portion thereof).

FIG. 3 depicts the durable housing 304 and the base plate 306 coupled together. For this particular embodiment, the durable housing 304 contains, among other components, a drive motor, a battery, a threaded drive shaft for the fluid reservoir, one or more integrated circuit chips and/or other electronic devices (not shown). The durable housing 304 and the base plate 306 are cooperatively configured to accommodate removable coupling of the durable housing 304 to the base plate 306. The removable nature of the durable housing 304 enables the patient to replace the fluid reservoir as needed.

Figure 4:
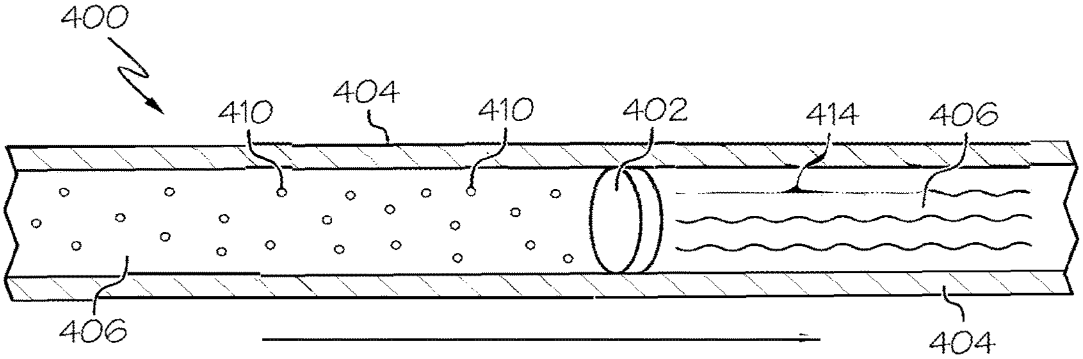
FIG. 4 is a schematic representation of a portion of a fluid conduit assembly.

The fluid delivery systems 200, 300 described here are merely two exemplary embodiments that can include a fluid conduit assembly outfitted with a gas trapping filter. In this regard, FIG. 4 is a schematic representation of a portion of a fluid conduit assembly 400 having a gas trapping filter 402 positioned therein. It should be appreciated that the fluid conduit assembly 400 has been simplified for ease of illustration. In practice, the fluid conduit assembly 400 may be realized in any of the fluid delivery systems described here, and/or in other fluid delivery systems not specifically described in detail here. For example, the fluid conduit assembly 400 may be implemented as, or form a part of, a fluid infusion set, a connector assembly, a fluid reservoir, a fluid reservoir cap, a chamber or internal feature of an infusion pump, or the like.

The fluid conduit assembly 400 is suitably configured to accommodate the delivery of a medication fluid such as insulin. The fluid conduit assembly 400 includes a structure 404 (or structures) defining a flow path 406 for the medication fluid. In FIG. 4, the structure 404 is depicted in cross section, and it resembles a tube. Alternatively, the structure 404 can be a section of a fluid connector (such as a two-part detachable connector), an internal feature of an infusion device, a portion of a fluid reservoir coupler, or the like. In certain embodiments, the structure 404 includes, forms a part of, or is realized as a reservoir cap for a fluid infusion device (see FIG. 6). In some embodiments, the structure 404 includes, forms a part of, or is integrated with an infusion set for a fluid infusion device. In this regard, the gas trapping filter 402 can be integrated with the delivery cannula hub or housing that is located at or near the downstream end of the infusion set. In yet other embodiments, the structure 404 includes, forms a part of, or is realized as a fluid connector, such as a LUER LOK fitting or connector. In certain embodiments, the structure 404 is implemented as a feature of the fluid infusion device. These and other deployments of the fluid conduit assembly 400 are contemplated by this disclosure, and the particular examples presented here are not intended to be limiting or exhaustive.

The flow path 406 is defined by the interior space of the structure 404. The gas trapping filter 402 may be coupled to the structure 404 and positioned in the flow path 406 such that the medication fluid passes through the gas trapping filter 402 during fluid delivery operations. FIG. 4 depicts a straightforward scenario where the gas trapping filter 402 physically obstructs the flow path 406, such that the medication fluid is not diverted around the gas trapping filter 402. In other embodiments, there can be additional fluid flow paths that allow some of the medication fluid to bypass the gas trapping filter 402.

The gas trapping filter 402 is formed from a suitable material, composition, or element such that the medication fluid can easily pass through the gas trapping filter 402 during fluid delivery operations. The gas trapping filter 402 can be formed from a hydrophilic, semi-hydrophilic, partially hydrophilic, or predominantly hydrophilic material. Although a truly hydrophilic material may be ideal, the material used for the gas trapping filter 402 can be partially or predominantly hydrophilic while exhibiting some amount of hydrophobicity. In practice, the gas trapping filter 402 can exhibit up to fifty percent hydrophobicity without adversely impacting the desired performance. For example, the gas trapping filter 402 may include or be fabricated from a hydrophilic membrane, a hydrophilic sponge material, or a hydrophilic foam material. As explained below, the gas trapping filter 402 also serves to filter particulates from the medication fluid during fluid delivery operations. Accordingly, the gas trapping filter 402 has a pore size that is small enough to inhibit the flow of particulates. In certain embodiments, the pore size is within the range of about 0.45 to 5.00 microns, which is suitable for most medical applications. Non-limiting examples of suitable materials for the gas trapping filter 402 include: polyacrylate; polyurethane; nylon; cellulose acetate; polyvinyl alcohol; polyethelene foam; polyvinyl acetate; polyester fiber felt; polyester (PET); polysulfone; polyethyl sulfone; collagen; polycaprolactone; or the like. It should be appreciated that the material or materials used to fabricate the gas trapping filter 402 can be treated to enhance the hydrophilic characteristics if so desired.

One function of the gas trapping filter 402 is to inhibit the downstream flow of air bubbles. Depending on the particular composition and configuration of the gas trapping filter 402, air bubbles 410 (depicted as small circles in the flow path 406 upstream of the gas trapping filter 402) can be blocked by the gas trapping filter 402 and/or retained within the gas trapping filter 402 as the liquid medication flows downstream. Thus, the gas trapping filter 402 may be realized as a gas impermeable membrane or material that also exhibits good hydrophilic properties. In some embodiments, the gas trapping filter 402 can be fabricated from material having micro-cavities formed therein for trapping and retaining gas bubbles from the medication fluid. FIG. 4 illustrates a scenario where the air bubbles 410 are removed from the medication fluid. Accordingly, no air bubbles 410 are present in the medication fluid that resides downstream from the gas trapping filter 402.

Another benefit of the gas trapping filter 402 relates to the volume accuracy of the fluid delivery system. In certain implementations, syringe pumps are calibrated to deliver a specified volume in response to a controlled mechanical actuation (e.g., movement of the syringe plunger in response to controlled rotation of an electric motor). Reducing or eliminating air from the fluid delivery path increases the accuracy of the volume calibrations.

In certain embodiments, the gas trapping filter 402 also serves to filter particulates from the medication fluid such that the particulate count of the downstream medication fluid is reduced. As mentioned above, the material used to fabricate the gas trapping filter 402 can be selected with a desired pore size to accommodate filtering of particulates having an expected size.

In some embodiments, the gas trapping filter 402 also serves to absorb and/or adsorb certain substances, chemicals, or suspended elements from the medication fluid. For example, the gas trapping filter 402 may include material that is configured or treated to absorb/adsorb lubricating or manufacturing oil that is associated with the manufacturing, assembly, or maintenance of one or more components of the fluid delivery system. In this regard, a fluid reservoir for insulin can be fabricated with a trace amount of silicone oil that serves as a lubricant for the plunger of the reservoir. Accordingly, the gas trapping filter 402 can include a material, layer, or treatment that reduces, traps, or otherwise removes some or all of the silicone oil from the medication fluid as it passes through the gas trapping filter 402.

In particular embodiments, the gas trapping filter 402 also serves as a drug depot during operation of the fluid delivery system. To this end, the gas trapping filter 402 can include a drug, medicine, chemical, or composition impregnated therein (or coated thereon, or otherwise carried by the gas trapping filter 402). A quantity of the drug is released into the medication fluid as the fluid flows through the gas trapping filter 402 during a fluid delivery operation. The wavy lines 414 in FIG. 4 schematically depict the drug after it has been released into the downstream medication fluid. In practice, the drug carried by the gas trapping filter 402 will eventually be depleted unless the gas trapping filter 402 or the fluid conduit assembly 400 is replaced before depletion. The drug carried by the gas trapping filter 402 can be selected to address the needs of the particular patient, fluid delivery system, medication fluid, etc. In accordance with the exemplary insulin infusion system described here, the gas trapping filter 402 is impregnated with a drug that treats the patient site to extend the useful life of the fluid infusion set. For example, the gas trapping filter 402 can be treated with an anticoagulant such as Heparin or Dextran. As another example, the gas trapping filter 402 can be impregnated or infused with an anti-proliferative drug such as Rapamycin. It should be appreciated that these examples are neither exhaustive nor restrictive, and that the gas trapping filter 402 can be impregnated, treated, or infused with any drug that may be appropriate and suitable for the particular medical condition, fluid delivery system, or application.

Although FIG. 4 shows a single component that serves as the gas trapping filter 402, an embodiment of the fluid conduit assembly 400 can utilize a plurality of physically distinct elements that collectively function as the gas trapping filter 402. For example, the gas trapping filter 402 can be fabricated from different materials that are selected for their properties and characteristics (gas trapping, oil absorption, oil adsorption, particulate filtering). Moreover, certain embodiments of the fluid delivery system can be outfitted with multiple gas trapping filters located in different sections of the fluid flow path. For example, one filter component can be positioned at or near the fluid reservoir, and another filter component can be positioned at or near the distal end of the fluid infusion set. These and other practical implementations are contemplated by this disclosure.

Figure 5:
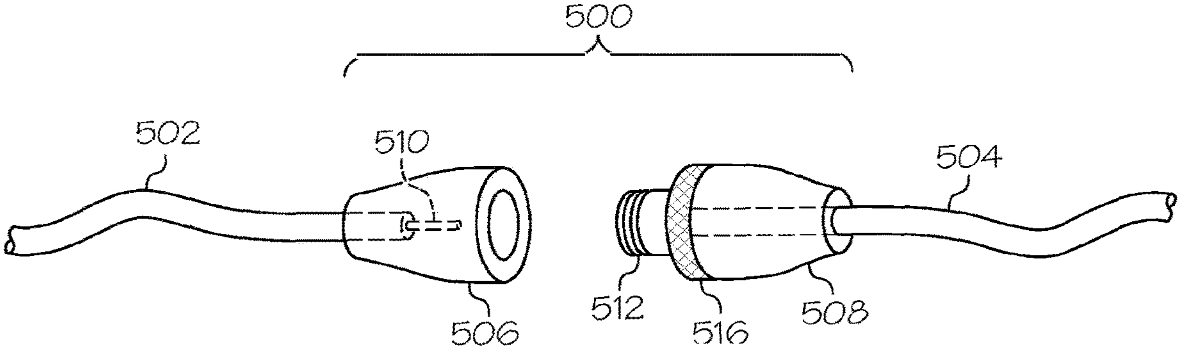
FIG. 5 is an exploded and partially phantom view of a connector assembly suitable for use with a fluid conduit.

As mentioned above, the fluid conduit assembly that carries the gas trapping filter can be realized in a number of different forms. For example, the fluid conduit assembly may include or be realized as a fluid connector, where the gas trapping filter is integrated in the fluid connector. In this regard, FIG. 5 is an exploded and partially phantom view of a fluid connector assembly 500 suitable for use with a fluid conduit assembly. The illustrated embodiment of the fluid connector assembly 500 functions to physically and fluidly couple an upstream section of tubing 502 to a downstream section of tubing 504. The fluid connector assembly 500 includes a first connector 506 (which is physically and fluidly coupled to the upstream section of tubing 502) that mates with a second connector 508 (which is physically and fluidly coupled to the downstream section of tubing 504). The first connector 506 includes a hollow needle 510 that provides a fluid flow path from the upstream section of tubing 502. The second connector 508 includes a septum 512 that receives the hollow needle 510 when the first connector 506 engages the second connector 508. When the two connectors 506, 508 are engaged and locked together, the medication fluid can flow from the upstream section of tubing 502, through the hollow needle 510, and into the downstream section of tubing 504.

One or both of the connectors 506, 508 can be provided with a gas trapping filter having the characteristics and functionality described previously. For this particular embodiment, a unitary gas trapping filter 516 is integrated in the second connector 508. The gas trapping filter 516 is located within the body of the second connector 508, and it resides downstream from the septum 512. During a fluid delivery operation, the medication fluid exits the hollow needle 510, enters the second connector 508 (e.g., into a space that is upstream from the gas trapping filter 516), and is forced through the gas trapping filter 516 before it passes into the downstream section of tubing 504.

Figure 6:
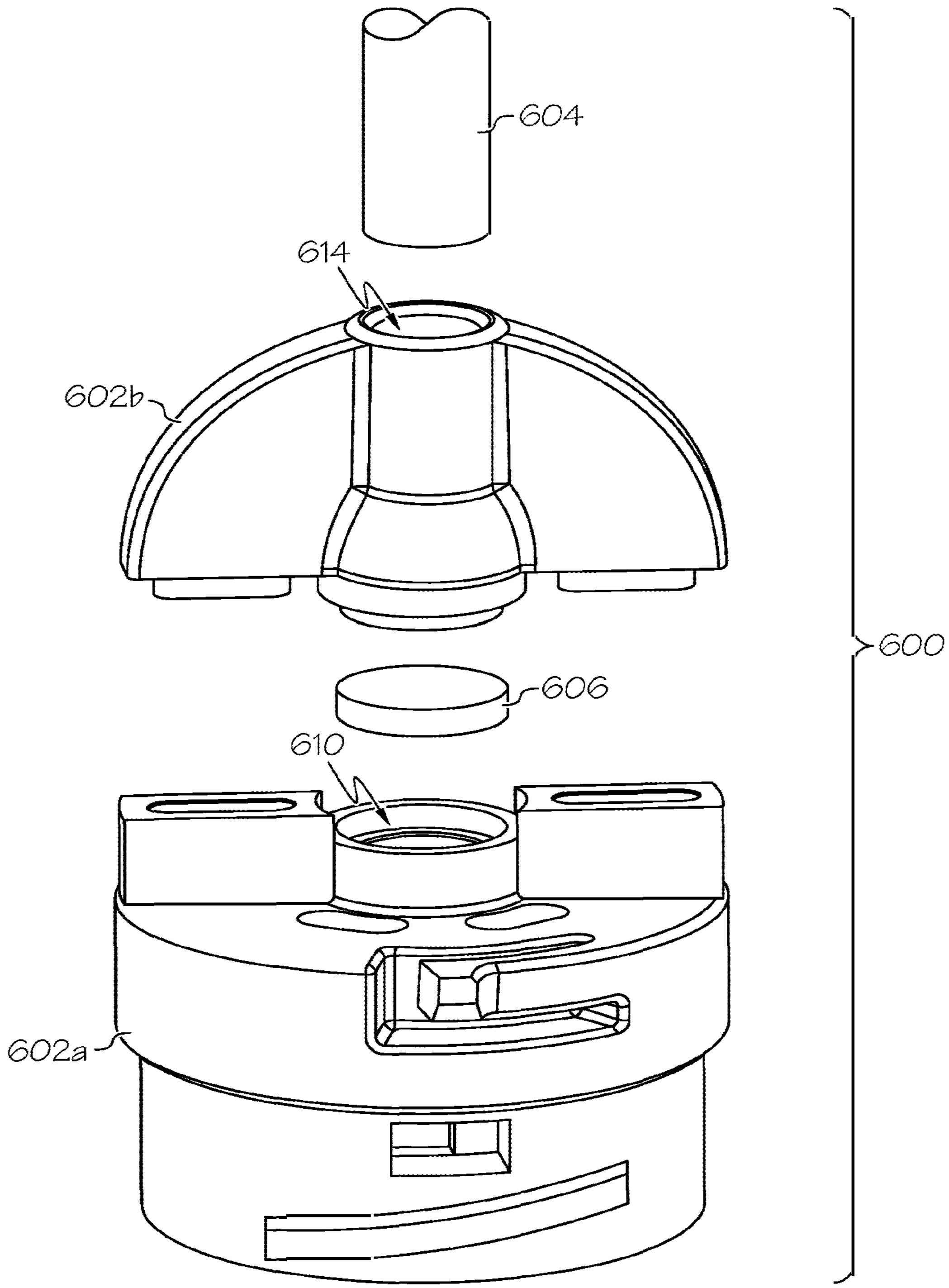
FIG. 6 is an exploded perspective view of an embodiment of a fluid conduit assembly that is realized as a cap for a fluid reservoir.

As another example, a fluid conduit assembly configured as described herein may include or be realized as an infusion set for a fluid infusion pump, where the gas trapping filter is integrated in the infusion set. In this regard, FIG. 6 is an exploded perspective view of a fluid conduit assembly that is realized as a cap or a connector assembly 600 for a fluid reservoir. In this regard, the connector assembly 600 is generally configured as described above for the connector assembly 214 shown in FIG. 2. Accordingly, the connector assembly 600 may be provided as component of a disposable infusion set.

The illustrated embodiment of the connector assembly 600 generally includes, without limitation: a body section 602; a flow path defined in the body section 602; a length of tubing 604 extending from the body section 602; and a gas trapping filter 606. FIG. 6 depicts the body section 602 separated into two constituent parts: a lower body section 602*a*; and an upper body section 602*b*. The lower body section 602*a* can be affixed to the upper body section 602*b* (for example, by sonic welding or using an adhesive) after installing the gas trapping filter 606 into a retaining cavity 610 formed within the lower body section 602*a*. In alternative embodiments, the body section 602 can be fabricated as a one-piece component by molding a suitable material while encapsulating the gas trapping filter 606 inside the body section 602.

The lower body section 602*b* is suitably configured to receive a fluid reservoir, e.g., by a threaded engagement, a snap fit, tabs, or the like. The tubing 604 is physically and fluidly coupled to the upper body section 602*b* such that the tubing 604 is in fluid communication with the flow path. This allows the tubing 604 to carry fluid from the body section 602 during a fluid delivery operation. The flow path, much of which is hidden from view in FIG. 6, may be defined by: a hollow needle that penetrates a septum of the fluid reservoir; an internal space, chamber, or conduit of the lower body section 602*a*, which is upstream of the gas trapping filter 606; and an internal space, chamber, or conduit 614 of the upper body section 602*b*, which is downstream of the gas trapping filter 606. The flow path continues into the tubing 604, which is connected to the upper body section 602*b*.

The gas trapping filter 606 is secured within the body section 602 such that it is positioned in the flow path of the medication fluid. During a fluid delivery operation, the medication fluid is forced out of the fluid reservoir and into the hollow needle (not shown in FIG. 6). The distal end of the hollow needle terminates at a location that is upstream of the gas trapping filter 606. This positioning ensures that the medication fluid can be filtered and otherwise treated by the gas trapping filter 606 before it exits the connector assembly 600. As explained above, the gas trapping filter 606 is suitably configured to reduce the amount of air bubbles in the downstream medication fluid, and to reduce the amount of particulates in the downstream medication fluid.

Figure 7:
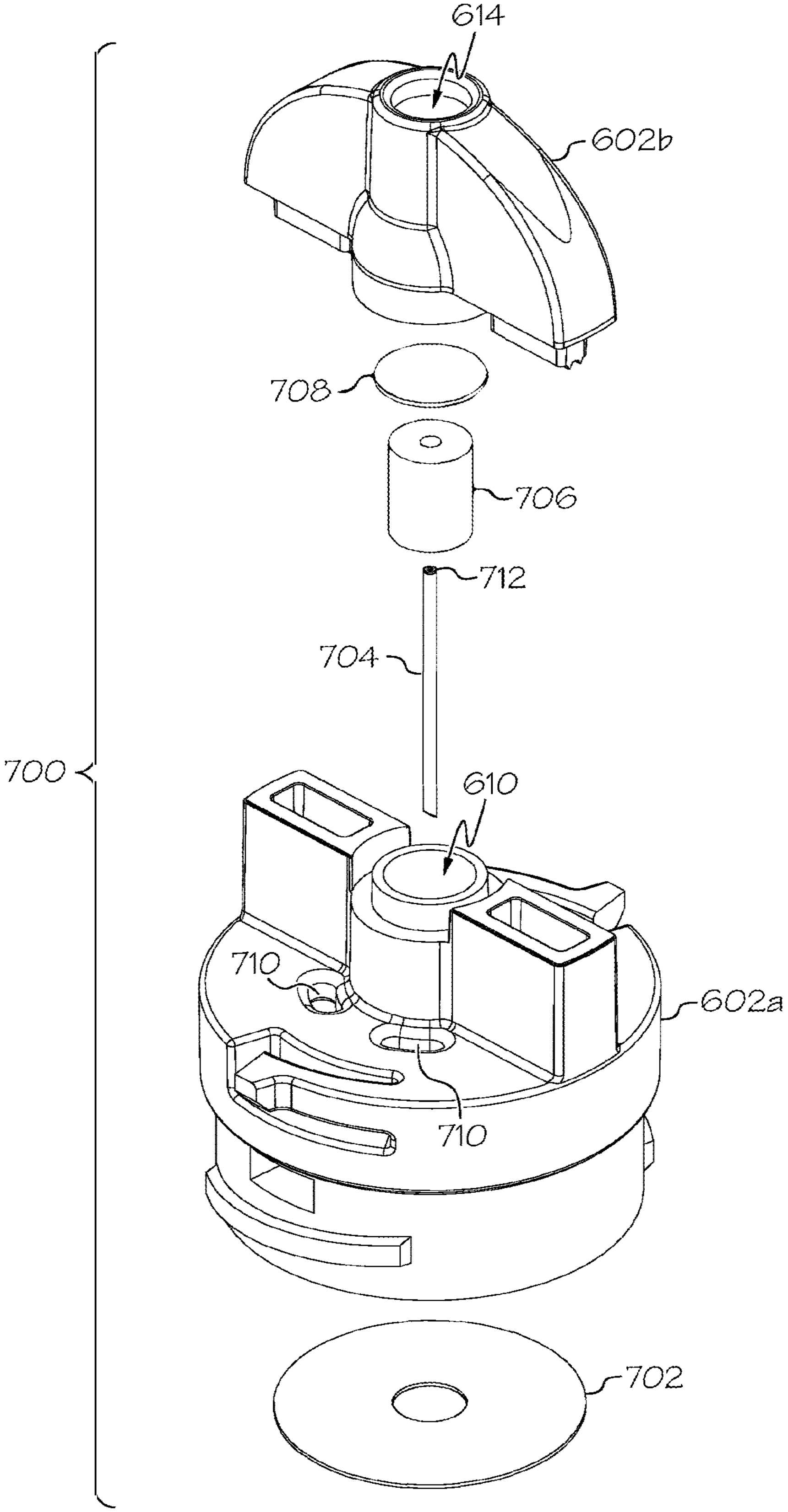
FIG. 7 is an exploded perspective view of another embodiment of a fluid conduit assembly that is realized as a cap for a fluid reservoir.

FIG. 7 is an exploded perspective view of another embodiment of a fluid conduit assembly 700 that is realized as a cap for a fluid reservoir. The assembly 700 shares some elements and features with the assembly 600 and, therefore, common elements and features will not be redundantly described here in the context of the assembly 700. As mentioned previously, the connector assembly 700 may be provided as component of a disposable infusion set.

The illustrated embodiment of the connector assembly 700 generally includes, without limitation: a body section 602 (having a lower body section 602*a* and an upper body section 602*b*); a venting membrane 702; a hollow needle 704; a gas trapping filter 706; and a reservoir membrane 708. These components can be assembled together in the manner generally described above for the assembly 600.

The venting membrane 702 can be affixed to the upper interior surface of the lower body section 602*a* such that the venting membrane 702 covers one or more vent holes 710 formed in the top portion of the lower body section 602*a*. The vent holes 710 facilitate venting of the reservoir chamber that resides in the housing of the fluid infusion device (see, for example, FIG. 2). The hollow needle 704 can be affixed to the lower body section 602*a* such that the downstream end 712 of the hollow needle 704 resides below or within the gas trapping filter 706 after the fluid conduit assembly 700 is fabricated. The positioning of the downstream end 712 is important to ensure that the medication fluid is forced through the gas trapping filter 706 during fluid delivery operations. The reservoir membrane 708 can be affixed within a cavity formed in the upper body section 602*b* (the cavity is hidden from view in FIG. 7). The reservoir membrane 708 is at least partially hydrophilic to allow the medication fluid to pass during fluid delivery operations.

The gas trapping filter 706 is secured within the body section 602 such that it is positioned in the flow path of the medication fluid. For the illustrated embodiment, the gas trapping filter 706 may be positioned between the reservoir membrane 708 and the downstream end 712 of the hollow needle 704. In certain embodiments, the gas trapping filter 706 is realized as a foam, sponge, or felt fiber composite material. Although not always required, the material used for the gas trapping filter 706 may include, without limitation: polyvinyl acetate (PVA); polyvinyl alcohol; polyester (PET); polycarbonate; polyurethane; polyethyl sulfone; collagen; polycaprolactone; or any combination thereof. In accordance with certain embodiments, a felt-based gas trapping filter 706 has a pore size within the range of about one to 100 microns, and preferably within the range of about 20 to 40 microns. In accordance with certain embodiments, a sponge-based gas trapping filter 706 has a pore size within the range of about 20 to 1000 microns. Regardless of its composition and configuration, the gas trapping filter 706 is suitably configured to reduce the amount of air bubbles in the downstream medication fluid, and to reduce the amount of particulates in the downstream medication fluid.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

We claim:

1. A fluid delivery system comprising:

a fluid infusion device comprising:

a housing;

a fluid reservoir configured to be received by the housing, wherein the fluid infusion device is configured to deliver a medication fluid from the fluid reservoir to a user, and wherein the fluid reservoir defines a first portion of a flow path for the medication fluid during fluid delivery operations;

a reservoir cap defining a second portion of the flow path for the medication fluid, wherein the reservoir cap comprises:

a lower body section to receive a portion of the fluid reservoir, the lower body section configured to couple with the housing of the fluid infusion device, and the lower body section configured to seal and secure the fluid reservoir inside a reservoir chamber that resides in the housing, a hollow needle in the lower body section, the hollow needle configured to carry fluid from the fluid reservoir into the lower body section, and an upper body section defining a conduit in fluid communication with the hollow needle, the upper body section configured to be positioned downstream of the lower body section along the flow path; and a gas trapping filter positioned in the flow path such that the medication fluid passes through the gas trapping filter during fluid delivery operations, wherein the gas trapping filter is configured to filter particulates from the medication fluid, and wherein the gas trapping filter is configured to physically obstruct the flow path such that the medication fluid is not diverted around the gas trapping filter.

2. The fluid delivery system of claim 1, wherein the gas trapping filter is formed from a polyvinyl alcohol material.

3. The fluid delivery system of claim 2, wherein the polyvinyl alcohol material is treated to enhance hydrophilic characteristics.

4. The fluid delivery system of claim 1, further comprising a reservoir membrane positioned along the flow path, downstream of the gas trapping filter.

5. The fluid delivery system of claim 1, wherein the gas trapping filter comprises a partially hydrophilic membrane, foam, sponge, felt, or fiber composite material.

6. The fluid delivery system of claim 1, wherein:

the gas trapping filter comprises a drug impregnated therein; and the gas trapping filter is configured such that, during a fluid delivery operation, a quantity of the drug is released into the medication fluid as the medication fluid flows through the gas trapping filter.

7. The fluid delivery system of claim 1, wherein the gas trapping filter has a pore size within the range of 20 to 1000 microns.

8. The fluid delivery system of claim 1, wherein the gas trapping filter comprises a plurality of physically distinct elements that collectively function as the gas trapping filter.

9. The fluid delivery system of claim 1, further comprising an infusion set configured to be fluidly coupled to the fluid infusion device.

10. The fluid delivery system of claim 1, further comprising a tubing defining a third portion of the flow path, wherein the tubing is configured to be fluidly coupled to the conduit of the upper body section of the reservoir cap.

11. The fluid delivery system of claim 10, further comprising an infusion unit configured to be worn by a patient and defining a fourth portion of the flow path, wherein a first end of the tubing is configured to be fluidly coupled to the reservoir cap and a second end of the tubing is configured to be fluidly coupled to the infusion unit.

12. The fluid delivery system of claim 1, wherein the medication fluid is insulin.

* * * * *